United States Patent
Wang

(10) Patent No.: US 9,850,533 B2
(45) Date of Patent: Dec. 26, 2017

(54) LIGASE REACTION MEDIATED AMPLIFICATION METHOD AND USE THEREOF

(71) Applicant: XIAMEN JIKE BIOTECHNOLOGY CO., LTD., Xiamen, Fujian (CN)

(72) Inventor: Xiabo Wang, Fujian (CN)

(73) Assignee: Xiamen Jike Biotechnology Co., Ltd., Xiamen, Fujian (CN)

(*) Notice: Subject to any disclaimer, the term of this patent is extended or adjusted under 35 U.S.C. 154(b) by 74 days.

(21) Appl. No.: 14/373,010

(22) PCT Filed: Jan. 18, 2013

(86) PCT No.: PCT/CN2013/000055
§ 371 (c)(1),
(2) Date: Jul. 17, 2014

(87) PCT Pub. No.: WO2013/107287
PCT Pub. Date: Jul. 25, 2013

(65) Prior Publication Data
US 2015/0004606 A1    Jan. 1, 2015

(30) Foreign Application Priority Data
Jan. 18, 2012 (CN) .......................... 2012 1 0015431

(51) Int. Cl.
*C12Q 1/68* (2006.01)

(52) U.S. Cl.
CPC ......... *C12Q 1/6862* (2013.01); *C12Q 1/6848* (2013.01)

(58) Field of Classification Search
None
See application file for complete search history.

(56) References Cited

U.S. PATENT DOCUMENTS

| | | | | |
|---|---|---|---|---|
| 5,914,230 A | * | 6/1999 | Liu | C12Q 1/6813 435/6.1 |
| 2007/0178445 A1 | * | 8/2007 | Eshleman | C12Q 1/6827 435/5 |
| 2010/0227320 A1 | * | 9/2010 | Fu | C12Q 1/6858 435/6.12 |
| 2014/0227683 A1 | * | 8/2014 | Cobb | C12Q 1/6818 435/5 |

FOREIGN PATENT DOCUMENTS

| | | | | |
|---|---|---|---|---|
| CN | 1824786 A | | 8/2006 | |
| CN | 102559661 A | | 7/2012 | |
| KR | WO 2006095981 A1 | * | 9/2006 | ........... C12Q 1/6848 |
| WO | WO 03048732 A2 | * | 6/2003 | ............... C12Q 1/68 |
| WO | 2005024053 A1 | | 3/2005 | |

OTHER PUBLICATIONS

Pont Kingdon et al. (Direct molecular haplotyping by melting curve analysis of hybridization probes: beta 2-adrenergic receptor haplotypes as an example, Nucleic Acids Res. Jun. 3, 2005;33(10):e89).*
Tobler et al. (The SNPlex Genotyping System: A Flexible and Scalable Platform for SNP Genotyping, J Biomol Tech. Dec. 2005;16(4):398-406).*

* cited by examiner

*Primary Examiner* — Aaron Priest
(74) *Attorney, Agent, or Firm* — Muncy, Geissler, Olds & Lowe, P.C.

(57) ABSTRACT

The reaction-medicated amplification methods and applications include a new type of ligase. The general amplification and detection of the downstream with the ligase reaction includes 3 linking probes. It achieves the effect of eliminating nonspecific signal interference by respectively filling the detection tag sequence, upstream primer tag sequence, and downstream primer combination tag sequence into 3 different linking probes. Wherein the linking probe containing detection tag sequence forms a cystic structure and the specific hybridization sequences on both sides of the cystic structure form a "hybridization community" when being hybrid to the target sequences. Being hybrid closely at the adjacent positions to the target sequences, 3 linking probes finally form a complete probe chain containing 3 "tag" sequences with the effect of ligase. This technique achieves the goals of reducing reaction background, enhancing signal-noise-ration and avoiding false positive.

3 Claims, 5 Drawing Sheets

SEQUENCE LISTING

<160> NUMBER OF SEQ ID NOS: 19

<210> SEQ ID NO 1
<211> LENGTH: 30
<212> TYPE: DNA
<213> ORGANISM: Artificial sequence
<220> FEATURE:
<223> OTHER INFORMATION: Synthesized

<400> SEQUENCE: 1
ctgcagggaa atgtctagat tggatcttgc    30

<210> SEQ ID NO 2
<211> LENGTH: 30
<212> TYPE: DNA
<213> ORGANISM: Artificial sequence
<220> FEATURE:
<223> OTHER INFORMATION: Synthesized

<400> SEQUENCE: 2
gcaagatcca atctagacat ttccctgcag    30

<210> SEQ ID NO 3
<211> LENGTH: 51
<212> TYPE: DNA
<213> ORGANISM: Artificial sequence
<220> FEATURE:
<223> OTHER INFORMATION: Synthesized

<400> SEQUENCE: 3
gcaagatcca atctaggaat ctggattcaa aatcttgaca tttccctgca g    51

<210> SEQ ID NO 4
<211> LENGTH: 51
<212> TYPE: DNA
<213> ORGANISM: Artificial sequence
<220> FEATURE:
<223> OTHER INFORMATION: Synthesized

<400> SEQUENCE: 4
gcaagatcca atctagacat ttggaatctg gattcaaaat cttccctgca g    51

<210> SEQ ID NO 5
<211> LENGTH: 51
<212> TYPE: DNA
<213> ORGANISM: Artificial sequence
<220> FEATURE:
<223> OTHER INFORMATION: Synthesized

<400> SEQUENCE: 5
gcaagatcca atctagacag gaatctggat tcaaaatctt tttccctgca g    51

<210> SEQ ID NO 6
<211> LENGTH: 19
<212> TYPE: DNA
<213> ORGANISM: Artificial sequence
<220> FEATURE:
<223> OTHER INFORMATION: Synthesized

<400> SEQUENCE: 6
gcaagatcca atctagaca    19

<210> SEQ ID NO 7
<211> LENGTH: 76
<212> TYPE: DNA
<213> ORGANISM: Artificial sequence

```
<220> FEATURE:
<223> OTHER INFORMATION: Synthesized

<400> SEQUENCE: 7
ctacacagtc tcctgtacct gggcaatatg atgctaccaa atttaagcag tatagcagac      60
atgttgagga atatga                                                      76

<210> SEQ ID NO 8
<211> LENGTH: 43
<212> TYPE: DNA
<213> ORGANISM: Artificial sequence
<220> FEATURE:
<223> OTHER INFORMATION: Synthesized

<400> SEQUENCE: 8
tggagcgacg atacgaagat atcatattcc tcaacatgtc tgc                        43

<210> SEQ ID NO 9
<211> LENGTH: 52
<212> TYPE: DNA
<213> ORGANISM: Artificial sequence
<220> FEATURE:
<223> OTHER INFORMATION: Synthesized

<400> SEQUENCE: 9
tatactgctt aaatttaact tcggtccttc atcgctggta gcatcatatt gc              52

<210> SEQ ID NO 10
<211> LENGTH: 42
<212> TYPE: DNA
<213> ORGANISM: Artificial sequence
<220> FEATURE:
<223> OTHER INFORMATION: Synthesized

<400> SEQUENCE: 10
ccaggtacag gagactgtgt agtctagata ggatcttgga gc                         42

<210> SEQ ID NO 11
<211> LENGTH: 21
<212> TYPE: DNA
<213> ORGANISM: Artificial sequence
<220> FEATURE:
<223> OTHER INFORMATION: Synthesized

<400> SEQUENCE: 11
tggagcgacg atacgaagat a                                                21

<210> SEQ ID NO 12
<211> LENGTH: 20
<212> TYPE: DNA
<213> ORGANISM: Artificial sequence
<220> FEATURE:
<223> OTHER INFORMATION: Synthesized

<400> SEQUENCE: 12
gctccaagat cctatctaga                                                  20

<210> SEQ ID NO 13
<211> LENGTH: 20
<212> TYPE: DNA
<213> ORGANISM: Artificial sequence
<220> FEATURE:
<223> OTHER INFORMATION: Synthesized
```

<400> SEQUENCE: 13
aacttcggtc cttcatcgct                                           20

<210> SEQ ID NO 14
<211> LENGTH: 49
<212> TYPE: DNA
<213> ORGANISM: Artificial sequence
<220> FEATURE:
<223> OTHER INFORMATION: Synthesized

<400> SEQUENCE: 14
tggagcgacg atacgaagat accaaatatt tttcgtaagt atttcaaat            49

<210> SEQ ID NO 15
<211> LENGTH: 47
<212> TYPE: DNA
<213> ORGANISM: Artificial sequence
<220> FEATURE:
<223> OTHER INFORMATION: Synthesized

<400> SEQUENCE: 15
agcaatggct cgtccatctc taaggcaagg ctctatggtt agtctca              47

<210> SEQ ID NO 16
<211> LENGTH: 47
<212> TYPE: DNA
<213> ORGANISM: Artificial sequence
<220> FEATURE:
<223> OTHER INFORMATION: Synthesized

<400> SEQUENCE: 16
agcaatggct cgtcaccttc cgtctgtact cgttatggtt agtctcg              47

<210> SEQ ID NO 17
<211> LENGTH: 41
<212> TYPE: DNA
<213> ORGANISM: Artificial sequence
<220> FEATURE:
<223> OTHER INFORMATION: Synthesized

<400> SEQUENCE: 17
cagccacatt ctcagaactg ctctagatag gatcttggag c                    41

<210> SEQ ID NO 18
<211> LENGTH: 19
<212> TYPE: DNA
<213> ORGANISM: Artificial sequence
<220> FEATURE:
<223> OTHER INFORMATION: Synthesized

<400> SEQUENCE: 18
catctctaag gcaaggctc                                             19

<210> SEQ ID NO 19
<211> LENGTH: 19
<212> TYPE: DNA
<213> ORGANISM: Artificial sequence
<220> FEATURE:
<223> OTHER INFORMATION: Synthesized

<400> SEQUENCE: 19
accttccgtc tgtactcgt                                             19

LIGASE REACTION MEDIATED AMPLIFICATION METHOD AND USE THEREOF

BACKGROUND OF THE INVENTION

Field of the Invention

This invention relates to an amplification method, particularly a reaction-medicated amplification method of ligase.

Nucleic acid testing (NAT) has been widely applied in the clinical diagnosis of molecular genetics, immunology, oncology, microbiology and other aspects. With the rapid development of molecular biology, some new methods of nucleic acid testing are constantly emerging, wherein the detection technique of ligase dependent is one of the categories. Ligase is an enzyme to close nicks on DNA or RNA chain, which can catalyst the reaction of 3'-end hydroxyl and 5'-end phosphate group of 2 single-stranded nucleic acid to form the phosphate diester bond with the aid of energy provided by NAD+ or ATP hydrolysis. The detection technique of ligase dependent is achieved mainly by the principles of nucleic acid hybridization and its fidelity at the nick junction. In 1988, Landegren firstly invented the in vitro mutation detection technique OLA of ligase, and applied it to identify the single-base difference between the mutant alleles $\beta^S$ and wild type alleles $\beta^A$ which encode $\beta$ globulin of causing Mediterranean sicklemia. In 1991, Barry extracted thermostable ligase and developed the techniques of LDR (ligase detection reaction) and LCR (ligase chain reaction). The raise of these two techniques has far-reaching significance to the development and application of the in vitro detection technique of ligase dependent, but each of them has nonspecific signal interference, poor usability and other problems. Thereafter, ligase reaction technique, combing with PCR technique, derives a series of new detection techniques, such as LDR/PCR, MLPA, PLP (padlock probe), MIP (molecular inversion probe), etc. These techniques conduct detection by achieving the "specific transformation" of the target genes by ligase reaction, and with the aid of the specific products after being amplified and transformed by PCR system. All these techniques present a relatively high detection flux, and can even achieve genotyping >10000 (MIP technique), however, they all have problems of serious nonspecific signal interference and false positive. The nonspecific signals of these techniques mainly come from: 1. nonspecific ligase reaction; 2. nonspecific PCR amplification. Influenced by the two non-specificities, the sensibility of the detection of LDR/PCR and MLPA techniques are limited; and even the nonspecific signals can be detected, the risk of false positive still exists. By adopting the method of exonuclease digesting the non-linked hybridization probes, PLR and MIP techniques eliminate the nonspecific amplification of the hybridization probes in PCR reaction to some extent; but when the detection of multiplicity is relatively high, the techniques will also be influenced by the nonspecific linking, and the presence of false positive is inevitable.

SUMMARY OF THE INVENTION

The technical problem to be solved in this invention is: provide an amplification method that can overcome ligase reaction and nonspecific signal interference of PCR. This technique achieves the objectives of reducing reaction background, enhancing signal-to-noise ratio, avoiding false positive and others.

In order to solve the problems claimed above, this invention provides a new type of reaction-mediated amplification method of ligase, meaning, to achieve the general amplification and detection of the downstream with the ligase reaction of 3 linking probes, which is characterized in that: each linking probe is consisted of the specific hybridization sequences and the filled tag sequences. Specifically, target sequence 7 are divided into segment A, B, C and D from its 3'-end to 5'-end, and linking probe a is consisted of the reversed complementary sequence 2 of Segment A and a length of upstream primer tag sequence 1, namely 2-1; linking probe b is consisted of the reversed complementary sequence 3' of Segment C, detection tag sequence 4 between Segment B and C, and the reversed complementary sequence 3 of Segment B, namely 3'-4-3; linking probe c is consisted of a length of downstream primer combination tag sequence 6 and the reversed complimentary sequence 5, namely 6-5; the claimed sequences 1, 4 and 6 are sequences which will not hybrid with the target sequences.

The respective design principles of the claimed upstream primer tag sequence 1, downstream primer combination sequence 6 and detection tag sequence 4 are: moderate GC content, 55-70° C. Tm value, 18-35 bp length, and with no relatively high homology with the target genome. No relatively high homology here means the homology is below 50%.

The claimed 2, 3, 3' and 5 have moderate GC content, 50-70° C. Tm value, and specific hybridization with the target sequences.

The claimed sequences of linking probe a, b and c, are all specific hybridization by eliminating sequence 1, 4 and 6.

This invention also provides a kit, containing the linking probes a, b and c, and the application of kit claimed above.

This invention also provides a chip, containing the linking probes a, b and c, and the application of chip claimed above.

Among the claimed segment A, B, C and D, there is no interval between each other.

The GC content of the target sequence is moderate, with no repetitive sequences or sequences with relatively high homology presenting. It's better not to have the presence of any SNP or mutation site at the specific hybridization points of linking probes; unless in the detection experiments of SNP or mutation, and the SNP or mutation sites are better located at the 3'-end of the linking probes.

This invention also relates to the application of a reaction-medicated amplification method of ligase.

The applications of the claimed kit, chip and reaction-medicated amplification method of ligase in the detections of gene sequence classification, quantification and others.

This invention detects the known target sequences, detectable mutation sites, SNP sites, qualitative and quantitative reactions of various species' target genes (such as the target DNA of bacteria and virus), etc.

This invention provides a new type of amplification method of ligase dependent-Omega probe technology. This method is to achieve the effect of eliminating nonspecific signal interference by respectively filling the detection tag sequence, upstream primer tag sequence, and downstream primer combination tag sequences into 3 different linking probes. We vividly call it Omega probe as the middle linking probe is similar in the form of "Ω", therefore, this method is called Omega probe technology.

This key component of Omega probe technology is the 3 linking probes. Each linking probe is consisted of specific hybridization sequences and the filled tag sequences. The tag sequences of the 3 linking probes are, respectively, upstream primer tag sequence of linking probe a, detection tag sequence of linking probe b, and downstream primer combination tag sequence of linking probe c (as shown in FIG. 1). The technical solution of this invention is to hybrid 3 linking probes at the adjacent positions to the target sequence, wherein the linking probe 6 forms a cystic structure when being hybrid to the target sequence (that is the filled detection tag sequence 4), and the specific hybridization sequences on the sides of the cystic structure form a "hybridization community". The 3 linking probes finally form a complete probe chain containing 3 "tag" sequences with the effect of ligase. And the linking products of this complete probe chain are to be amplified by the general PCR system.

The methods and procedures of this invention are: fully denature genomic DNA template with high temperature (98° C., 5-10 minutes), conduct specific hybridization between the 3 linking probes and the to-be detected gene locus DNA sequences (hybrid at the adjacent position to DNA sequences), conduct ligation with thermostable enzyme (such as Ampligase<Epicentre>, Tag DNA ligase<NEB>, etc.), and then form a complete strand of linking probe. This step of reaction aims to convert the target DNA into a complete probe after ligation. The second step is to spontaneously amplify the linked complete probes with a couple of universal primers. The unlinked probes cannot be amplified normally, or they will present linear amplification (the linking probe on the right side presents linear amplification) or nonspecific amplification (the nonspecific combination of probe on the right or left side and primers amplifies nonspecific products). And as there is no primer tag sequence and primer combination tag sequence on both ends of the Omega probe which lead the detection reaction, it will not present nonspecific amplification. And as there is no non-specific signal detected in the system, therefore, there is no nonspecific signal interference.

Upstream primer tag sequences and downstream primer combination sequences come from the universal primer sequences. In one of the embodiments of this invention, upstream universal primer F is the sequence:

```
                                    (SEQ ID NO: 11)
          TGGAGCGACGATACGAAGATA;
``` and downstream universal primer R is the sequence:

```
                                    (SEQ ID NO: 12)
          GCTCCAAGATCCTATCTAGA.
```

This invention is a new type of reaction-medicated amplification method of ligase. Different from the traditional amplification methods depending on ligation (such as LDR/PCR, MLPA, PLP, MIP, etc.), this technology has the following advantages:

1. It designs 3 linking probes against a to-be detected gene sequence in order to guarantee the extremely high specificity of the detection reaction, and it's especially suitable for the resolution and detection of sequences with a relatively high homology;

2. It eliminates the interference of nonspecific linking signals: the linking products of this technology present either linear amplification or a small amount of index amplifications in PCR, but none of these products can be detected;

3. It avoids the interference of nonspecific amplification signals: linking probe b will not present nonspecific amplification, while the little nonspecific amplification between linking probes a, c and PCR primers cannot be detected;

4. It add tag sequences into all the 3 linking probes, which help to achieve the efficient amplification and detection of different target sequences in the same amplification system and detection system;

5. Its experiment process and operation time are short, and detection system is open, allowing the detection with the real-time PCR system, chip system, and others.

6. The length of the linking probe is relatively short (about 35-60 nt), which is easy to design and chemically synthesize.

DETAILED DESCRIPTION OF THE DRAWINGS

Figure 1:
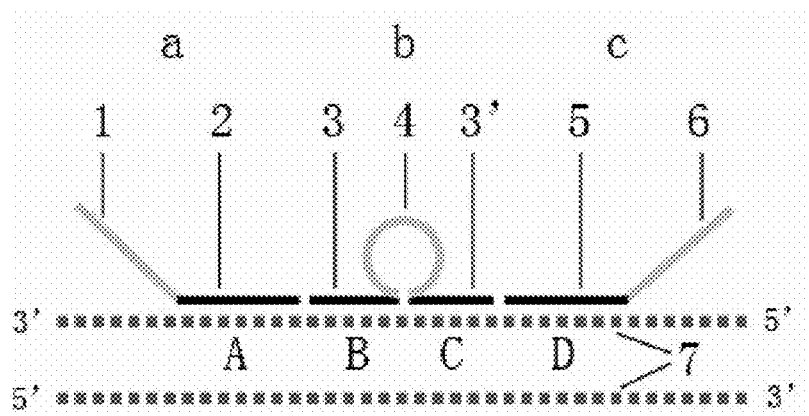
FIG. 1 is a schematic view of an illustration showing the detection principle of this new type of reaction-medicated amplification method of ligase, wherein 7 is the target sequence. The target sequence is from 3'-end to 5'-end, and is divided into A, B, C and D in turn. 1 is the upstream primer tag sequence, 2 is the reversed complimentary sequence of segment A, 3 is the reversed complimentary sequence of segment B, 3' is the reversed complimentary sequence of segment C, 4 is the detection tag sequence between segment B and C, 5 is the reversed complimentary sequence of segment D, and 6 is the downstream primer combination tag sequence.
Figure 2A:
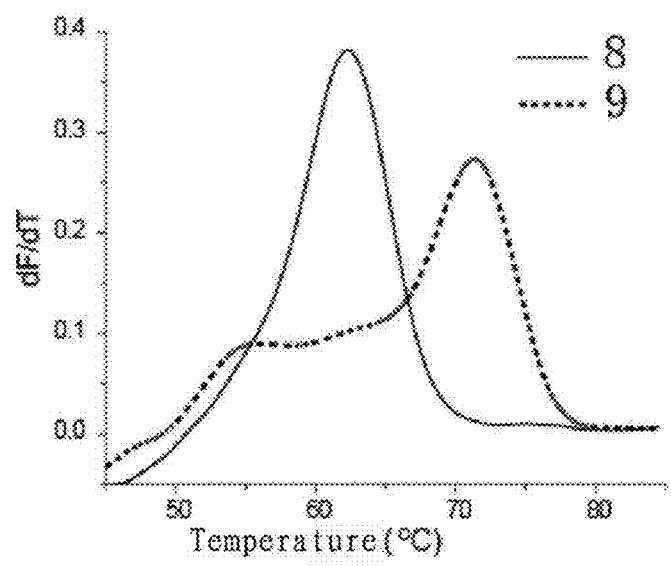
FIGS. 2A, 2B and 2C are all graph illustrations of the ordinary and cystic structural hybridization sequence melting curve graphs, wherein 8 are linking probes, 2 are melting curves, 9 is the linking probe 1 melting curve, 10 is the linking probe 3 melting curve, 11 is the linking probe 4 melting curve, 12 is the linking probe 2 melting curve, 13 is the linking probe 4 melting curve, and 14 is the linking probe 5 melting curve.
Figure 2B:
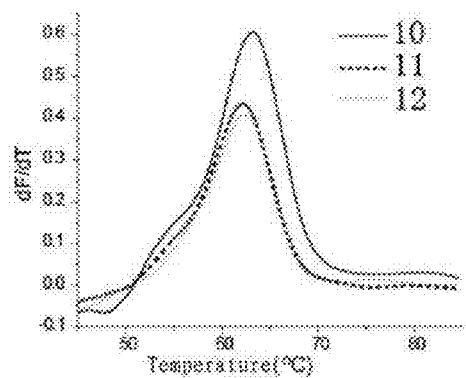
Figure 2C:
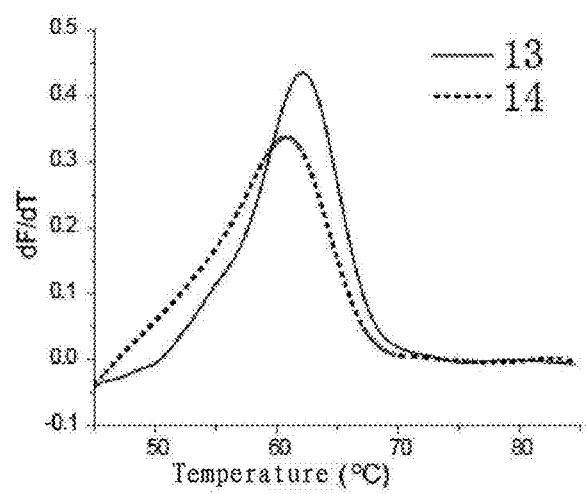

The embodiments of this invention will be described in detail with embodiments in the following. However, as the technical personnel in this field will understand, the following embodiments are only to introduce this invention, but should not be regarded as to define the scope of this invention. Any part in the embodiments, indicated with no specific technologies or conditions, should be conducted according to the technologies or conditions described in the literatures of this field (such as in Reference: J. Same Brooke et al. Huang Yian et al (translators). The Experimental Guide of Molecular Cloning, third edition. Science press.), or product instructions. The applied reagents or instruments, indicated with no manufacturer, are all conventional products that can be purchased in the public market.

The applied instruments in the embodiments: real-time fluorescence PCR (Rotor-gene 600, QIAGEN, Germany), ultraviolet visible spectrophotometer (ND-1000, NanoDrop, the United States), and benchtop microcentrifuge (Eppendorf, Germany). All the synthesized sequences in the embodiments of this invention are from Sangon Biotech. Ligase is AmpligaseDNA Ligase Kit (5 U/Ml, 1000 U, Epicentre). The applied genomic DNA samples, all acquired by using DNeasy™ Blood Kit from Oiagen, are from peripheral blood extraction from average people, according to the extraction methods in the instructions. Peripheral blood samples are provided by Xiamen Matemal and Child Health Hospital. All the applications of samples have obtained the permissions from the parties involved or their guardians.

Embodiment 1: Melting Curve Comparison Among Multiple Linking Probes

Target sequence:

(SEQ ID NO: 1)
CTGCAGGGAAATGTCTAGATTGGATCTTGC

Linking probe 1 (completely complimentary hybridization with the target sequence):

(SEQ ID NO: 2)
GCAAGATCCAATCTAGACATTTCCCTGCAG

Linking probe 2 (hybrid with the target sequence to form a cystic structural hybridization community, with the cystic structure in the middle; base in the dotted-line part constitutes a cystic structure):

(SEQ ID NO: 3)
GCAAGATCCAATCTAGGAATCTGGATTCAAAATCTTGACATTTCCCTGCAG

Linking probe 3 (hybrid with the target sequence to form a cystic structural hybridization community; base in the dotted-line part constitutes a cystic structure):

(SEQ ID NO: 4)
GCAAGATCCAATCTAGACATTTGGAATCTGGATTCAAAATCTTCCCTGCAG

Linking probe 4 (hybrid with the target sequence to form a cystic structural hybridization community; base in the dotted-line part constitutes a cystic structure):

(SEQ ID NO: 5)
GCAAGATCCAATCTAGACAGGAATCTGGATTCAAAATCTTTTTCCCTGCAG

Linking probe 5:

(SEQ ID NO: 6)
GCAAGATCCAATCTAGACA

Observe the melting process of the claimed linking probes and the target sequence with Sybrgreen dye.

25 μL melting systems include: 75 mmol/L Tris-HCl pH 9.0, 20 mmol/L $(NH_4)_2SO_4$, 0.01% Tween 20, 50 mmol/L KCl, 4 mmol/L $Mg^{2+}$, 0.4 μmol/L linking probes, 0.2 μmol/L target sequence, and 0.2 μL Sybrgreen fluorochrome. The melting analysis procedures include: 95° C. for 1 minute; 40° C. for 1 minute; heat up the temperature from 40° C. to 90° C., and collect the corresponding fluorescence signals throughout the entire heating process.

Results show: 1. See the ordinary and cystic structural hybridization sequence melting curve graph 2A, wherein 8 is the linking probe 2 melting curve, and 9 is the linking probe 1 melting curve. The melting curve of linking probes 1 and 2 after being hybrid with the target sequence shows: the melting of cystic structural probes, the same as that of ordinary probes, is an independent melting process rather than the respective melting process on both sides of a cystic structure, whose melting peak is an independent unimodal. The Tm value of cystic structural probe is about 8° C. lower than that of other normal probes. 2. See the ordinary and cystic structural hybridization sequence melting curve graph 2B, wherein 10 is the linking probe 3 melting curve, 11 is the linking probe 4 melting curve, and 12 is the linking probe 2 melting curve. The melting curve of linking probes 2, 3 and 4 after being hybrid with the target sequence shows: the position of the cystic structure in the probe affects the Tm value of hybridization, and when it is in the middle of the probe, the Tm value of the corresponding "hybridization community" reaches its minimum. 3. See the ordinary and cystic structural hybridization sequence melting curve graph 2C, wherein 13 is the linking probe 4 melting curve, 14 is the linking probe 5 melting curve. The melting curve of linking probes 4 and 5 after being hybrid with the target sequence shows: the hybridization Tm value of the cystic structure is higher than that of a single side, further illustrating the holistic melting phenomenon of cystic structural probes.

Embodiment 2: Quantitative Detection of Target Sequences

Select a segment of synthesized DNA sequence as the object of the study, design 3 linking probes against the sequence and respectively hybrid them on the adjacent positions to the target sequence:

Target sequence:

(SEQ ID NO: 7)
CTACACAGTCTCCTGTACCTGGGCAATATGATGCTACCAAATTTAAGCAG
TATAGCAGACATGTTGAGGAATATGA

Linking probe a:

(SEQ ID NO: 8)
TGGAGCGACGATACGAAGATATCATATTCCTCAACATGTCTGC

Linking probe b:

(SEQ ID NO: 9)
PO4-TATACTGCTTAAATTTAACTTCGGTCCTTCATCGCTGGTAGCATCAT
ATTGC

Linking probe c:

(SEQ ID NO: 10)
PO4-CCAGGTACAGGAGACTGTGTAGTCTAGATAGGATCTTGGAGC

Wherein the upstream primer tag sequence of linking probe a is the universal primer F sequence, and the downstream primer combination tag sequence of linking probe c is the reversed complimentary sequence of universal primer R:

(SEQ ID NO: 11)
Universal primer F: TGGAGCGACGATACGAAGATA (SEQ ID NO: 12)
Universal primer R: GCTCCAAGATCCTATCTAGA The detection tag sequence of the linking probe in the middle is the FAM-tagged Taqman probe sequence (FAM-AACTTCGGTCCTTCATCGCT-BHQ, sequence part is SEQ ID NO: 13). The 3 linking probes are hybrid on the adjacent positions to the target sequence. And the goal of quantitative detection is achieved by PCR amplification after ligase reaction.

Target sequence obtains DNA with content of $1.0\cdot10^7$, $1.0\cdot10^6$, $1.0\cdot10^5$, $1.0\cdot10^4$, $1.0\cdot10^3$ and $1.0\cdot10^2$ copy respectively by ten-time gradient dilution. Select the DNA at this gradient as the template of quantitative detection.

Experiment systems: 1. Ligation: 10 μL reaction systems include 1 μL hybridization linking buffer solution, 25 fmol linking probes, 1 u ligase, 5 μL DNA template; ligation procedures include 95° C. for 1 minute, 60° C. for 10 minutes, 55° C. for 10 minutes, and 50° C. for 10 minutes. 2. PCR reaction: 25 μL reaction systems include 2 μL linking products of the first step, 75 mmol/L Tris-HCl pH 9.0, 20 mmol/L $(NH_4)_2SO_4$, 0.01% Tween 20, 50 mmol/L KCl, 1 u Tag enzyme, 3 mmol/L $Mg^{2+}$, 0.2 μmol/L Tagman probe, 0.4 μmol/L universal primer F and 0.4 μmol/L universal primer R; PCR reaction procedure includes 95° C. for 3 minutes, 95° C. for 15 seconds, 58° C. for 30 seconds, 50 cycles: and collect fluorescence signals throughout the process of annealing extension at 58° C.

Figure 3A:
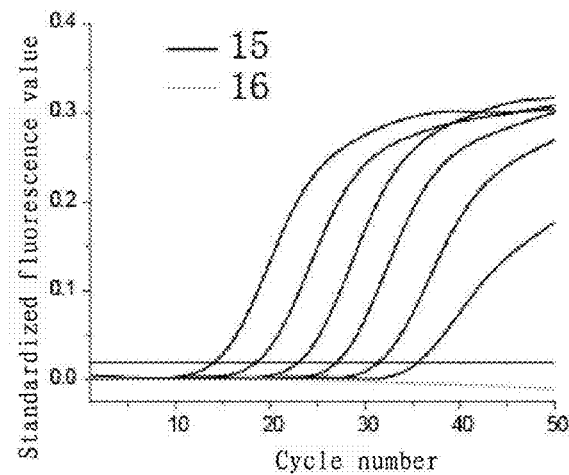
FIGS. 3A and 3B are graph illustrations of the amplification curve of gradient diluting DNA and the standard curve of gradient diluting DNA, respectively; wherein 15 is the amplification curve of the gradient dilution template (sample amounts are placed in order from left to right, respectively, $1.0 \times 10^7$, $1.0 \times 10^6$, $1.0 \times 10^5$, $1.0 \times 10^4$, $1.0 \times 10^3$ and $1.0 \times 10^2$ copy), 16 is the amplification curve of negative control.
Figure 3B:
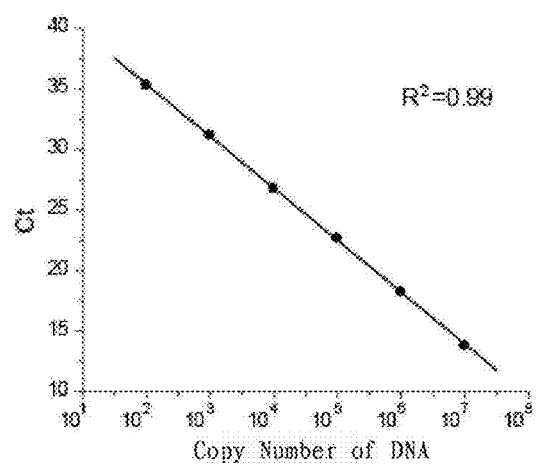

Amplification curve of gradient dilution template is: all FAM channels present amplification signals with amplification curve presenting gradient, and Ct value of the amplification curve (the corresponding cycle number when the fluorescence signals in the PCR reaction tubes reach its set threshold) is gradually increasing with the reduction of template copy number. NTC (negative control) presents no amplification signal (as shown in FIG. 3A). Standard curve of gradient dilution template is: its Ct value and the logarithm of starting copy number present a good linear relationship (R2=0.99), indicating the good quantitative ability of this method (as shown in FIG. 3B).

Embodiment 3: SNP Genotyping Results of 3 Human Genomic DNA Samples

Select the SNP site (rs740598) as the object of the study and design 4 linking probes as follow:
Linking probe a:

(SEQ ID NO: 14)
TGGAGCGACGATACGAAGATACCAAATATTTTTCGTAAGTATTTCAAAT

Linking probe b-1:

(SEQ ID: 15)
PO4-AGCAATGGCTCGTCCATCTCTAAGGCAAGGCTCTATGGTTAGTCTCA

Linking probe b-2:

(SEQ ID NO: 16)
PO4-AGCAATGGCTCGTCACCTTCCGTCTGTACTCGTTATGGTTAGTCTCG

Linking probe c:

(SEQ ID NO: 17)
PO4-CAGCCACATTCTCAGAACTGCTCTAGATAGGATCTTGGAGC

Wherein the tag sequences of linking probes a and c are the same according to Embodiment 1; the detection sequence of linking probe b-1 is FAM-tagged Taqman probe sequence (FAM-CATCTCTAAGGCAAGGCTC-BHQ, sequence part is SEQ ID NO: 18), correspondingly being hybrid to template whose genotype is A; the detection sequence of linking probe b-2 is TET-tagged Taqman probe sequence (TET-ACCTTCCGTCTGTACTCGT-BHQ, sequence part is SEQ ID NO: 19), correspondingly being hybrid to the template whose genotype is G. Linking probe a and c are hybrid on the adjacent positions on both sides of linking probe b. The goal of genotyping is achieved by PCR amplification after ligase reaction.

Select 3 human genomic samples with known genotypes (each concentration is 10 ng/μL) as the validating objects. Genotype of sample A is AA, sample B GG, and sample C AG.

Experiment systems: 1. Genomic DNA denaturation: take 5 μL of each genome (50 ng in total) and put them into warm bath at 98° C. for 5 minutes, then lower the temperature to 25° C. and preserve the genomes; 2. Ligation: 10 μL reaction systems include 1 μL hybridization linking buffer solution, 25 fmol linking probes, 1 u ligase, 5 μL denatured genomic templates at the step 1; ligation procedures includes 95° C. for 1 minutes, 60° C. for 10 minutes, 55° C. for 10 minutes, and 50° C. for 10 minutes; 3. PCR reaction: 25 μL reaction systems include 2 μL linking products from step 2, 75 mmol/L Tris-HCl pH 9.0, 20 mmol/L $(NH_4)_2SO_4$, 0.01% Tween 20, 50 mmol/L KCl, 1 u Tag enzyme, 3 mmol/L $Mg^{2+}$, 0.15 μmol/L of each Tagman probe, 0.4 μmol/L universal primer F and 0.4 μmol/L universal primer R; PCR reaction procedures include 95° C. for 3 minutes, 95° C. for 15 seconds, 58° C. for 30 seconds, 50 cycles; and collect two-colored fluorescence signals of FAM and TET throughout the process of annealing extension at 58° C.

Figure 4A:
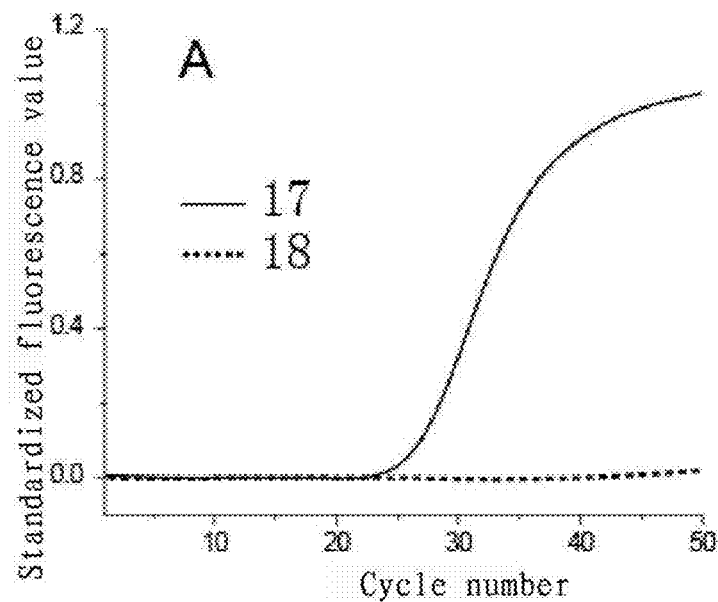
FIGS. 4A, 4B and 4C are graph illustration, showing, respectively, the SNP genotyping results of 3 human genomic DNA samples, wherein 17 is FAM channel signal, corresponding to genotype A; 18 is HEX channel signal, corresponding to genotype G.
Figure 4B:
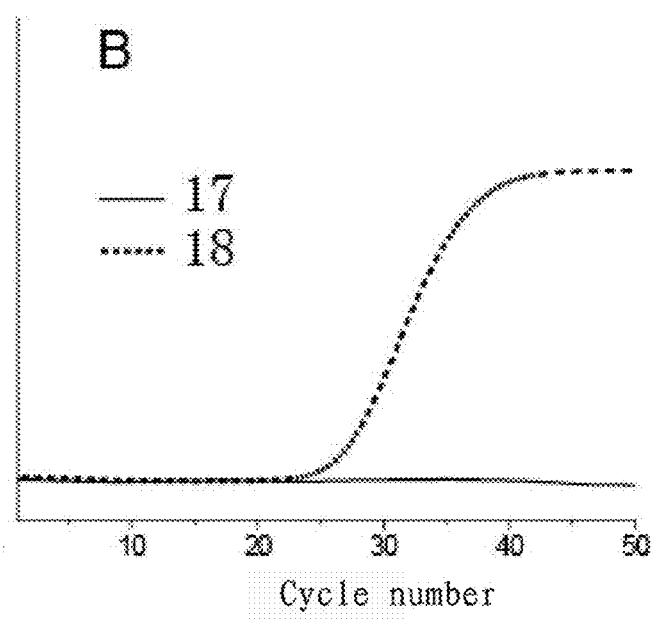
Figure 4C:
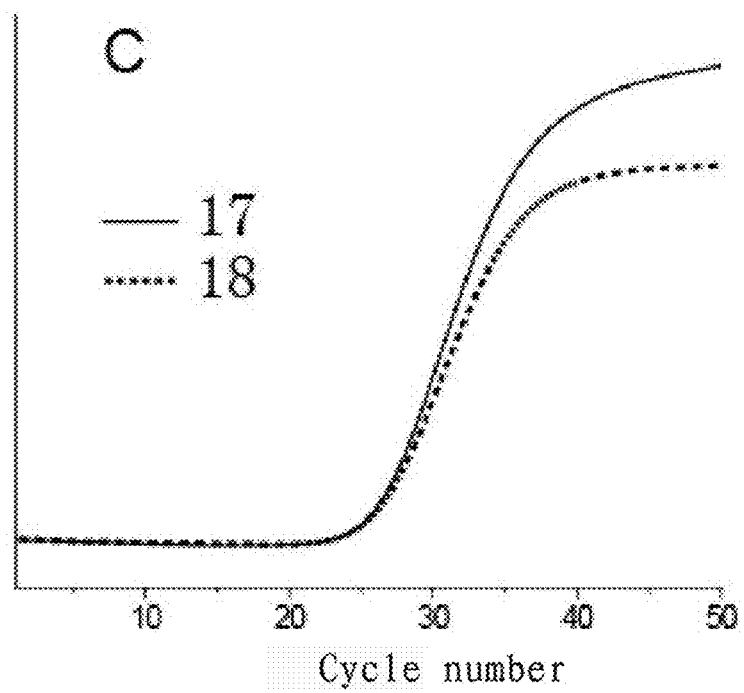

See FIG. 4A for SNP genotyping results of sample A, the amplification curve of sample A is: FAM (Green) channel (namely 17) presents amplification signals, while TET (Yellow) channel (namely 18) presents no amplification signal, therefore, verifying its corresponding SNP site as AA type. See FIG. 4B for SNP genotyping results of sample B, the amplification curve of sample B is: FAM (Green) channel presents no amplification signal, while TET (Yellow) channel presents amplification signals, therefore, verifying its corresponding SNP site as GG type. See FIG. 4C for SNP genotyping results of sample C, the amplification curve of sample C is: FAM (Green) presents amplification signals, and TET (Yellow) channel also presents amplification signals, therefore, verifying its corresponding SNA site as AG type.

I claim:

1. A method for detecting a target sequence using ligase chain reactions, the method comprising:
   selecting the target sequence as a template;
   dividing the target sequence in an order of segment A, segment B, segment C, and segment D from one end to another end of the target sequence, wherein a length of each of segment A and segment D is 8-42 nt, and wherein the length of segment B is 8-21 nt, and wherein the length of segment C is 8-21 nt;
   providing a first linking probe, the first linking probe including a first reverse complement of the segment A and an upstream primer tagging sequence;
   providing a second linking probe, the second linking probe including a third reverse complement of the segment C, a detection tagging sequence between the segment B and the segment C, and a second reverse complement of the segment B, wherein the detection tagging sequence is: 55-70° C. Tm value, and 18-35 bp length; and the detection tagging sequence forms a cystic structure when hybridized to the target sequence;
   providing a third linking probe, the third linking probe including a downstream primer combination tagging sequence and a fourth reverse complement of the segment D;
   forming a probe chain with three linking probes, the first, the second, and the third linking probes in a ligation chain reaction with the effect of ligase;
   amplifying the probe chain with a plurality of universal primers; and
   providing a detection probe comprising a sequence complementary to the detection tagging sequence:
   wherein the upstream primer tagging sequence, the detection tagging sequence, and the downstream primer combination tagging sequence do not hybridize with the target sequence; and
   wherein there is no primer tagging sequence and primer combination tagging sequence on both ends of the second linking probe which leads to a detection reaction, and wherein there is no nonspecific amplification; wherein the detection tagging sequence is based on hybridizing the detection probe to the detection tagging sequence.

2. The method according to claim 1, wherein the upstream primer tagging sequence, the downstream primer combination sequence, and the detection tagging sequence meet the following conditions: a melting temperature of 55-70° C., a length of 18-35 nt, and a homology with a target genome below 50%.

3. The method according to claim 1, wherein the first, the second, the third, and the fourth reverse complements meet the following conditions: a melting temperature of 55-70° C. and specific hybridization with the target sequences.

* * * * *